United States Patent
Zezula et al.

(10) Patent No.: US 10,457,671 B2
(45) Date of Patent: Oct. 29, 2019

(54) CRYSTALLINE FORM OF CANAGLIFLOZIN AND A METHOD OF ITS PREPARATION

(71) Applicant: Zentiva k.s., Prague (CZ)

(72) Inventors: Josef Zezula, Polna (CZ); Peter Babiak, Presov (CZ); Ondrej Dammer, Hostivice (CZ)

(73) Assignee: Zentiva k.s., Prague (CZ)

( * ) Notice: Subject to any disclaimer, the term of this patent is extended or adjusted under 35 U.S.C. 154(b) by 0 days.

(21) Appl. No.: 15/776,794

(22) PCT Filed: Oct. 27, 2016

(86) PCT No.: PCT/CZ2016/000119
§ 371 (c)(1),
(2) Date: May 17, 2018

(87) PCT Pub. No.: WO2017/084644
PCT Pub. Date: May 26, 2017

(65) Prior Publication Data
US 2018/0327395 A1    Nov. 15, 2018

(30) Foreign Application Priority Data
Nov. 20, 2015 (CZ) .................. 2015-824

(51) Int. Cl.
*C07D 409/10* (2006.01)
*B01D 9/00* (2006.01)

(52) U.S. Cl.
CPC ......... *C07D 409/10* (2013.01); *B01D 9/0054* (2013.01); *B01D 9/0063* (2013.01)

(58) Field of Classification Search
CPC ... B01D 9/0054; B01D 9/0063; C07D 409/10

USPC .............................................................. 549/6
See application file for complete search history.

(56) References Cited

U.S. PATENT DOCUMENTS

| | | | | |
|---|---|---|---|---|
| 2008/0146515 A1 * | 6/2008 | Nomura | ............ | A61K 31/7034 514/23 |
| 2009/0233874 A1 * | 9/2009 | Abdel-Magid | ...... | C07D 409/10 514/23 |

FOREIGN PATENT DOCUMENTS

| | | | | |
|---|---|---|---|---|
| CN | 104230907 | | 12/2014 | |
| CN | 104230907 A | * | 12/2014 | .......... C07D 409/10 |
| CN | 104530023 | | 4/2015 | |
| CN | 104530023 A | * | 4/2015 | .......... C07D 409/10 |
| WO | WO 2009/035969 | | 3/2009 | |
| WO | WO 2014/180872 | | 11/2014 | |

OTHER PUBLICATIONS

ICH Harmonised Tripartite guidelines (Year: 1999).*
Caira M.R. "Crystalline Polymorphism of Organic Compounds", Jan. 1, 1998, Topics in Current Chemistry, Springer, Berlin, DE, vol. 198, p. 163-208, XP001156954, ISSN:0340-1022, DOI:10.1007/3-540-69178-5_5.

* cited by examiner

*Primary Examiner* — Rita J Desai
(74) *Attorney, Agent, or Firm* — Pearl Cohen Zedek Latzer Baratz LLP

(57) ABSTRACT

The invention relates to a new crystalline form of Canagliflozin of formula I, with its systematic name (2S,3R,4R,5S, 6R)-2-(3-((5-(4-fluorophenyl)thiophen-2-yl) methyl)-4-methylphenyl)-6-(hydroxymethyl)tetrahydro-2H-pyran-3,4, 5-triol5 and a method of its preparation.

15 Claims, 1 Drawing Sheet

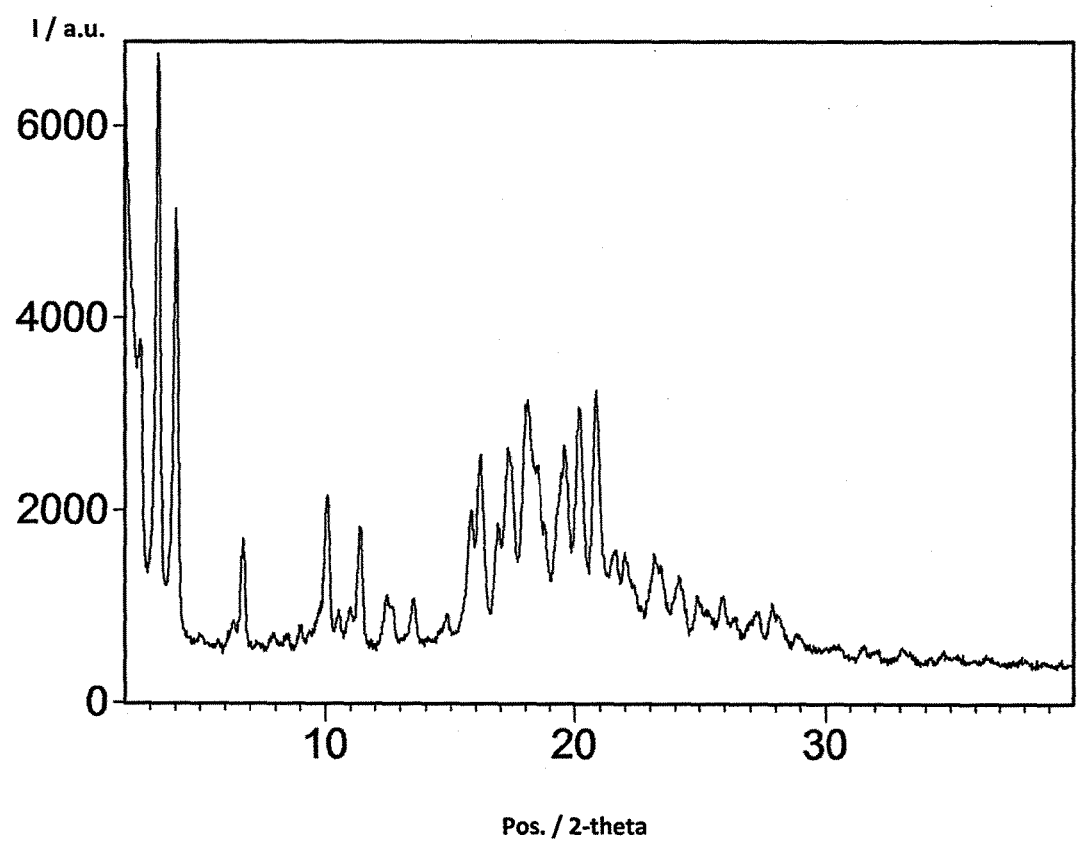

CRYSTALLINE FORM OF CANAGLIFLOZIN AND A METHOD OF ITS PREPARATION

CROSS-REFERENCE TO RELATED APPLICATIONS

This application is a National Phase Application of PCT International Application No. PCT/CZ2016/000119, International Filing Date 27 Oct. 2016, claiming priority of Czech Patent Application No. PV 2015-824, filed 20 Nov. 2015, which is hereby incorporated by reference.

FIELD OF THE INVENTION

The invention relates to a new crystalline form of Canagliflozin of formula I, with its systematic name (2S,3R,4R,5S,6R)-2-(3-((5-(4-fluorophenyl)thiophen-2-yl)methyl)-4-methylphenyl)-6-(hydroxymethyl)tetrahydro-2H-pyran-3,4,5-triol and a method of its preparation.

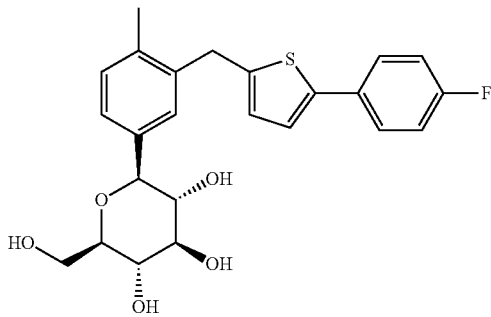

(I)

BACKGROUND ART

Canagliflozin (I) is a SGLT-2 inhibitor used for the treatment of diabetes (Chao, E.C. Drugs Fut. 2011, 36(5), 351) acting by blocking the re-absorption of glucose in the kidneys and its excretion in the urine.

The selection of a suitable polymorphic form of the active substance is very important because it influences its solubility, chemical stability, purification effect during isolation, mechanical properties as the particle size etc., which are important during the preparation of drug forms.

Therefore, new forms of Canagliflozin are still being looked for and discovered with the aim to control solubility, chemical stability, purification effect during crystallization or to ensure suitable mechanical properties.

The patent of the company Mitsubishi Tanabe WO2008069327A1 describes and claims a crystalline form of canagliflozin hydrate and a process of its preparation. This polymorph is characterized by the XRPD 2θ CuK$_\alpha$ diffraction peaks: 4.36, 13.54, 16.00, 19.32, 20.80

The following patent of the companies Janssen and Mitsubishi WO2009035969A1 describes preparation of the crystalline hydrate I-S and also claims a tetraacetyl derivative of canagliflozin. There, the form I-S is characterized by the following XRPD 2θ CuK$_\alpha$ diffraction peaks: 3.9 8.0 9.7 10.9 13.0 13.9 15.5 15.6 15.9 16.2 17.3 18.3 18.7 18.8 19.1 19.4 20.3 20.9 21.1 21.8 22.5 22.7 23.2 23.4 25.1 25.7 26.3 26.8

Further, cocrystals of canagliflozin with L-proline and citric acid have been described (WO-2012154812, Janssen Pharmaceutica).

The patent application WO 2013064909 of the company SCINOPHARM claims five crystalline complexes and an amorphous form of Canagliflozin. Namely: Form CS1—complex with L-proline (1:1), form CS-2—complex with D-proline (1:1), form CS-3—complex with L-phenylalanine (1:1), form CS4—complex with D-proline (1:1) obtained by heating (125° C.) of form CS-2 or another complex with D-proline (1:1) and form CS-5 obtained by heating of form CS-4.

The patent application WO2014180872 of the company LEK PHARMACEUTICALS describes and claims non-stoichiometric hydrates of Canagliflozin prepared by suspending of the API in water and drying in an environment with controlled humidity. Form HxA, characterized by the XRPD 2θ CuK$_\alpha$ diffraction peaks: 5.4±0.2°, 6.7±0.2°, 13.2±0.2°, 16.1 ±0.2°, 19.6±0.2° and form HxB, which is characterized by the XRPD 2θ CuK$_\alpha$ diffraction peaks: 6.6±0.2°, 7.3±0.2°, 12.2±0.2°, 15.4±0.2°, 19.9±0.2°.

The application WO 2015071761 of the company CRYSTAL PHARMATECH describes and claims three crystalline forms referred to as B, C, D. Form B is characterized by the XRPD 2θ CuK$_\alpha$ diffraction peaks: 6.3 9.4 11.7 12.6 16.9 18.2 19.9 22.3 24.4 28.9. Form C is characterized by the XRPD 2θ CuK$_\alpha$ diffraction peaks: 6.5, 9.8, 13.4, 16.4, 17.1, 19.5, 19.8, 23.7 25.2 26.5 and finally form D is characterized by the XRPD 2θ CuK$_\alpha$ diffraction peaks: 6.8 10.2 13.6 16.5 17.1 18.5 19.2 20.5 22.9 24.4.

The application CN 103641822A of the company Faming Zhuanli Shenqing describes a form characterized by the XRPD 2θ CuK$_\alpha$ diffraction peaks: 3.86, 15.46, 17.30, 18.80, 19.10 and 20.26, which however seems to be identical to the form from the patent WO2009035969 according to XRPD.

Another application CN 103980261 A of UNIVERSITY TIANJIN; QILU describes the crystalline form A and its preparation. Form A is characterized by the XRPD 2θ CuK$_\alpha$ diffraction peaks: 3.7, 3.9, 7.7, 7.9, 11.5, 13.1, 13.5, 14.3, 15.5, 17.3, 18.8, 19.3, 20.3, 22.5, 22.7, 23.2 and 23.4.

Preparation of an eutectic mixture of Canagliflozin and L-phenylalanine is described by the application CN 103965267 AO (priority CN2013128068 20130124) of the company JIANGSU HANSOH PHARMACEUTICAL.

The application CN 103936725 A (20140723) of Faming (priority CN20141129127 20140401) describes form C and a method of its preparation. Form C is characterized by the XRPD 2θ CuK$_\alpha$ diffraction peaks: 3.4, 6.5, 12.7, 15.8, 19.8, 24.3, 24.8 and 29.1.

The patent application CN 103936726 A (priority CN20141155712 20140418) of the company SUZHOU JINRAN PHARMACEUTICAL TECHNOLOGY CO LTD describes and claims crystalline forms III and IV and methods of their preparation. Form III—complex with octanol is characterized by the XRPD 2θ CuK$_\alpha$ diffraction peaks: 6.61, 3.92 and 19.68 and form IV—an anhydrate prepared by washing of form III with n-heptane, filtering and drying under reduced pressure is characterized by the XRPD 2θ CuK$_\alpha$ diffraction peaks: 17.40, 15.35 and 14.91.

The patent application CN104119323 (A) of the company CHONGQING PHARM RES INST CO describes and claims an amorphous form and a process of its preparation. The amorphous form is characterized by a DSC (Differential Scanning Calorimetry) endothermic peak in the temperature range of 53-63° C. and has characteristic absorption peaks at the wavelengths of approx. 832 cm$^{-1}$ and 809cm$^{-1}$ in the infrared spectrum.

The patent application CN 104230907 A of the company Faming Zhuanli Shenqing describes and claims a crystalline form and its use.

The patent application WO2014195966 (A2) of the company Cadila describes and claims a stable amorphous form and a process of its preparation and a solid solution of this API and a process of its preparation. Specific polymers for the preparation of solid solutions are mentioned (HPMC-AS, HPMC, copolymers of methacrylic acid, PVP).

Another patent application of the company Zentiva CZ PV 2014-634 describes and claims complexes of canagliflozin and cyclodextrins and methods of their preparation. These complexes can be advantageously used for stabilization of amorphous canagliflozin from the chemical and polymorphic stability point of view. β-cyclodextrin, modified β-cyclodextrins and γ-cyclodextrin were mainly used for the complexation of canagliflozin.

DISCLOSURE OF THE INVENTION

An object of the invention is a new stable crystalline form of the active pharmaceutical ingredient (API) canagliflozin, referred to as X-C, characterized by these characteristic reflections in the X-ray powder pattern: 3.3; 10.1; 18.0 and 20,8±0.2° 2-theta, which were measured with the use of CuKα radiation.

This form also shows more characteristic reflections: 4.0; 6.7; 11.4; 16.2; 17.3; 19.5 and 20.2±0.2° 2-theta.

This form is especially advantageous from the point of view of preparation of highly pure Canagliflozin and exhibits good chemical stability and suitable solubility for the use for the production of pharmaceutical preparations.

Another object of the invention is a method of preparation of this form directly from a solution of crude Canagliflozin prepared using the Zemplén reaction (Zemplén, G.; Kuntz, A. *Chem. Ber.* 1924, 57B, 1357) of the corresponding tetraacetyl derivative. Preparation of form X-C through recrystallization of Canagliflozin from an etheric solvent in the pure form or with an addition of an alcohol and/or saturated hydrocarbon is also claimed.

DETAILED DESCRIPTION OF THE INVENTION

Polymorph X-C in accordance with this invention is characterized by the XRPD pattern presented in table 1.

TABLE 1

XRPD - characteristic diffraction peaks of form X-C of Canagliflozinu

| Pos. [°2 Th.] | Interplanar distance [A] = 0.1 nm | Rel. Int. [%] |
| --- | --- | --- |
| 2.56 | 34.494 | 23.8 |
| 3.33 | 26.508 | 100.0 |
| 4.03 | 21.926 | 78.1 |
| 6.70 | 13.183 | 20.0 |
| 10.06 | 8.783 | 25.2 |
| 11.38 | 7.771 | 22.4 |
| 12.44 | 7.107 | 8.5 |
| 13.49 | 6.559 | 8.0 |
| 14.80 | 5.981 | 3.6 |
| 15.78 | 5.612 | 21.6 |
| 16.18 | 5.474 | 30.7 |
| 16.87 | 5.252 | 16.4 |
| 17.32 | 5.116 | 32.7 |
| 18.04 | 4.915 | 37.4 |
| 18.48 | 4.798 | 26.3 |

TABLE 1-continued

XRPD - characteristic diffraction peaks of form X-C of Canagliflozinu

| Pos. [°2 Th.] | Interplanar distance [A] = 0.1 nm | Rel. Int. [%] |
| --- | --- | --- |
| 19.51 | 4.546 | 30.7 |
| 20.17 | 4.399 | 37.5 |
| 20.84 | 4.259 | 44.5 |
| 21.53 | 4.124 | 9.5 |
| 22.06 | 4.026 | 12.6 |
| 23.13 | 3.843 | 9.9 |
| 24.14 | 3.684 | 10.9 |
| 24.89 | 3.574 | 6.6 |
| 25.89 | 3.439 | 8.5 |
| 27.18 | 3.278 | 6.3 |
| 27.83 | 3.204 | 6.2 |
| 28.90 | 3.087 | 3.0 |

Another object of this invention is a preparation method of the polymorph X-C wherein crystalline or amorphous Canagliflozin is dissolved in a suitable etheric solvent selected from cyclopentyl methyl ether, t-butyl methyl ether or 2-methyltetrahydrofuran, possibly also with an addition of a C1-C5 saturated aliphatic linear or branched alcohol and the obtained solution is either cooled down and/or in the hot state an antisolvent is added that is selected from the group of heptane, cyclohexane, hexane and then the solution is cooled down and the crystallized product is isolated. The dissolution and distillation are advantageously carried out under an inert atmosphere of e.g. dry nitrogen.

To reduce the thermal loading of the product the distillation operations should also preferably be carried out at a reduced pressure.

In a preferred embodiment according to this invention, Canagliflozin is dissolved in cyclopentyl methyl ether under reflux conditions and the water contained in it is removed by azeotropic distillation and the solution is then desaturated by addition on n-heptane and then cooled to the laboratory temperature with or without adding of an inoculation crystal of form X-C. The crystallized product is then isolated with the use of well-known techniques.

In another preferred embodiment according to this invention, Canagliflozin is dissolved under reflux conditions in t-butyl methyl ether with or without addition of t-butanol and the water contained in it is removed by azeotropic distillation and the solution is then cooled to the laboratory temperature with or without adding of an inoculation crystal of form X-C. The crystallized product is then isolated with the use of well-known techniques.

Another object of this invention is a preparation method of the polymorph X-C from a solution of crude Canagliflozin obtained by deacetylation of the tetraacetyl derivative of formula II under the Zemplén conditions (Zemplén, G.; Kuntz, A. *Chem. Ber.* 1924, 57B, 1357) consisting in adjustment of pH, replacement of the solvent with an ether that is immiscible with water (from the group of cyclopentyl methyl ether, t-butyl methyl ether or 2-methyltetrahydrofuran) by distillation, washing with water and azeotropic drying. The solution prepared this way, possibly with an addition of a suitable antisolvent (from the n-heptane, n-hexane or cyclohexane group) or cosolvent (from the group of linear or branched C1-C5 alcohols (e.g. t-butanol) is then cooled with or without adding of an inoculation crystal of form X-C, see Diagram 1. The separated crystals are then isolated and dried using standard procedures.

Diagram 1:

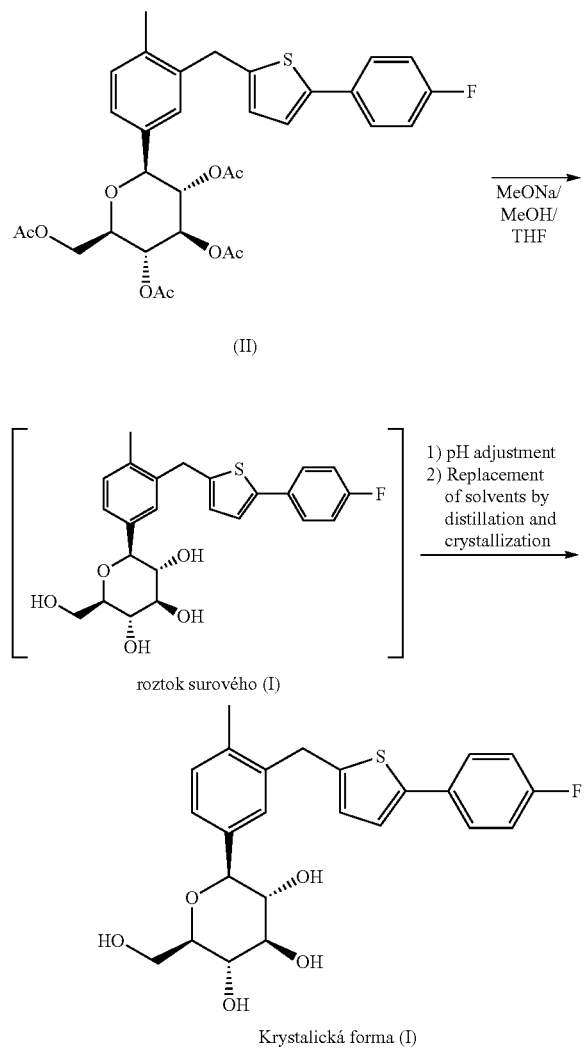

BRIEF DESCRIPTION OF THE DRAWINGS

FIG. 1: X-ray powder pattern of crystalline form X-C of Canagliflozin.

LIST OF ANALYTICAL METHODS

Measurement parameters of XRPD: The diffractograms were measured using an X'PERT PRO MPD PANalytical diffractometer, used radiation CuKα (λ=1.542 Å), excitation voltage: 45 kV, anode current: 40 mA, measured range: 2-40° 2θ, increment: 0.01° 2θ. For the measurement a flat powder sample was used that was placed on a Si plate. For the setting of the primary optical equipment programmable divergence slits with the irradiated area of the sample of 10 mm, 0.02 rad Soller slits and a ¼ anti-diffusion slit were used. For the setting of the secondary optical equipment an X'Celerator detector with maximum opening of the detection slot, 0.02 rad Soller slits and a 5.0 mm anti-diffusion slit were used.

HPLC determination of chemical purity: column Ascentis Express C18, detection 215.0 nm:

| | Eluent A: Water B: Acetonitrile Gradient: | | |
|---|---|---|---|
| Time (min) | Flow (ml/min) | % A | % B |
| 0.0 | 1.0 | 65 | 35 |
| 1.0 | 1.0 | 55 | 45 |
| 4.0 | 1.0 | 52 | 48 |
| 5.0 | 1.0 | 22 | 78 |
| 7.0 | 1.0 | 12 | 88 |
| 8.0 | 1.0 | 5 | 95 |
| 10.0 | 1.0 | 5 | 95 |
| 10.5 | 1.0 | 65 | 35 |
| 12.0 | 1.0 | 65 | 35 |

EXAMPLES

Example 1

A suspension of crystalline Canagliflozin hemihydrate (5.53 g, HPLC 99.60%) in cyclopentyl methyl ether (CPME, 100 ml) was heated to boiling under a nitrogen atmosphere, being mechanically stirred, and the obtained solution was concentrated by distillation at the atmospheric pressure—12 ml of an azeotropic mixture of CPME-H$_2$O was removed by distillation. The solution was then cooled down to 85° C. and then heptane (30 ml) was slowly added under stirring and the obtained solution was then slowly cooled down to the laboratory temperature during approx. 3 h; at the temperature of 40° C. a seed of the polymorph X-C (prepared in advance in the same solvent system) was added. The obtained thick suspension of crystals was stirred for 1 h and then the crystals were filtered off, washed with heptane (2×25 ml), pre-dried with aspirated air on glass frit (0.5 h) and then dried in a vacuum drier (90° C./18 kPa/20 h). The amount of 4.57 g of yellowish crystals of the polymorphic form X-C was obtained (83% yield, HPLC 99.70%, residual solvents: CPME 0.17%, heptane 0.043%), having the melting point of 94.5-98.3° C.

Example 2

A suspension of Canagliflozin hemihydrate (1.0 g, HPLC 99.60%) in t-butyl methyl ether (MTBE, 45 ml) was heated up to boiling under stirring under a nitrogen atmosphere and 17 ml of an azeotropic mixture of MTBE-H$_2$O was removed by distillation, then t-butanol (3 ml) was added under reflux conditions and the obtained solution was slowly cooled down to the laboratory temperature while being stirred and it was further stirred for two days. The obtained crystals were then filtered off and exposed to aspirated air for 1 h and then they were dried in a vacuum drier (50° C./18kPa). The amount of 0.61 g of a white crystalline substance—polymorph X-C was obtained (61% yield, HPLC 99.86%, residual solvents: 2.63% of MTBE, 1.20% of t-BuOH).

Example 3

The tetraacetate II (5 g, HPLC 99.52%) was suspended in 100 ml of MeOH and the suspension was cooled under stirring in an ice bath to 3° C. under a nitrogen atmosphere. Then, a solution of MeONa in MeOH (25% wt., 2.3 ml, 1.0 equiv.) was added by dripping. The stirred reaction mixture was further cooled for 0.5 h and then it was left to heat up to the laboratory temperature (hereinafter RT, 23° C.). After 3.5 h of stirring at RT the input substance disappeared (HPLC analysis) and a solution was obtained. 50 ml of 10% citric acid was added to the reaction mixture and the reaction mixture was concentrated on a rotary vacuum evaporator (RVE, 40° C./20 mbar). After the evaporation of MeOH, CPME (70 ml) was added to the concentrate and the mixture was washed twice with 70 ml of water and the organic phase was dried over $MgSO_4$ and filtered. Being stirred under a nitrogen atmosphere, the solution was heated up to 80° C. and heptane (30 ml) was slowly added to it by dripping and the solution was left to slowly cool down to RT overnight. After 17 hours the separated crystals were aspirated and washed with 25 ml of heptane and dried in a vacuum drier (50° C./20 kPa) for 24 h. The amount of 2.57 g of the white crystalline polymorph X-C of Canagliflozin I was obtained (yield 70%, HPLC 99.4%, residual solvents after 24 of drying: 0.31% of heptane, 0.82% of CPME). The crystals were further dried for another day (HPLC 99.5%, residual solvents: 0.27% of heptane, 0.73% of CPME).

Example 4

200 ml of MeOH and 10 g of the tetraacetate II were put in a reactor with the content of 11 under $N_2$ and the stirred suspension was cooled down to 0° C. Then, 4.6 ml of a solution of MeONa MeOH (25% wt. solution) was added by dripping and the reaction mixture was stirred at the temperature of 0° C. for 0.5 h. Then, the reaction mixture was slowly heated up to RT during 0.5 h. After 2 h of stirring at RT the input substance disappeared (HPLC analysis) and a solution was obtained. 150 ml of 10% citric acid and 150 ml of CPME were added to the reaction mixture. The reaction mixture was then heated up to 70° C. and 250 ml of the solvent was removed by distillation. 100 ml of water and 100 ml of CPME were added to the residue and the mixture was stirred for 10 minutes. The aqueous phase was then separated and the organic CPME phase was washed with 100 ml of water under stirring for 20 min. Then, for better separation of phases the mixture was heated up to 40° C. The aqueous phase was separated and another 100 ml of CPME was added to the organic phase. After that, the organic phase was dried by means of azeotropic distillation at a reduced pressure (45° C. mixture temperature/20 kPa). Approx. 100 ml of the solvents were removed by distillation. Then, the solution was diluted with 30 nil of CPME and heated up to 80° C. and 64 ml of heptane was added by dripping until slight turbidity was achieved. The turbidity was clarified by adding of 1 ml of CPME and several inoculation crystals of form X-C were added and the solution was cooled down to RT during 0.5 h and left to be stirred for 16 h and the separated crystals were filtered off and washed with heptane (2 ×30 ml) and dried in a vacuum drier (50° C./20 kPa) for 24 h. The amount of 6.15 g of the white crystalline polymorph X-C of Canagliflozin I was obtained (yield 79%, HPLC 99.7%, residual solvents: 0.65% of heptane, 1.5% of CPME). Extended drying (24 h) provided a product with the purity of 99.6%, HPLC, residual solvents: 0.57% of heptane, 1.4% of CPME, melting point 98.7-99.8° C.

Example 5

Canagliflozin (5 g, HPLC 99.60%) was dissolved in 40 ml of CPME and dried by means of azeotropic distillation at the atmospheric pressure (approx. 30 ml removed by distillation) and slowly cooled down to RT and left to be stirred at the laboratory temperature for 3 days. The thick suspension of crystals was then diluted with 16 ml of CPME and stirred for 24 h, the crystals were then aspirated and dried in a vacuum drier (50° C./20 kPa, 2 days). The amount of 4.50 g of the white crystalline polymorph X-C of Canagliflozin I was obtained (yield 90%, HPLC 99.70%, residual solvents: 0.52% CPME, melt. point 95.7-97.2° C.).

Example 6

Canagliflozin (5 g, HPLC 99.60%) was dissolved in 50 ml of 2-MeTHF and dried by means of azeotropic distillation at the atmospheric pressure (approx. 20 ml removed by distillation) under a nitrogen atmosphere and slowly cooled down to RT and left to be stirred at the laboratory temperature for 16 h. The solution was heated up to 80° C. in a bath and n-heptane (26 ml) was added to it under stirring until slight turbidity was achieved, which was removed by adding of 2-MeTHF (1 ml) and the solution was slowly cooled down to the laboratory temperature under stirring. At the temperature of approx. 35° C., an inoculation crystal was added and the mixture was stirred under nitrogen for 3 days. A thick suspension of crystals was then diluted with 10 ml of 2-MeTHF and 10 ml of n-heptane and the crystals were aspirated, washed with n-heptane (30 ml) and dried with aspirated air for 3 days. The drying then continued in a vacuum drier (80° C./10-15 kPa, 22 h). The amount of 4.39 g of the white crystalline polymorph X-C of Canagliflozin I was obtained (yield 88%, HPLC 99.70%, residual solvents: 0.25% of n-heptane, 0.05% of 2-MeTHF).

The invention claimed is:

1. A crystalline form X-C of Canagliflozin of formula I, comprising characteristic reflections in an X-ray powder pattern measured with the use of CuKα radiation, wherein said characteristic reflections are set forth in Table 1

TABLE 1

XRPD—characteristic diffraction peaks of form X-C of Canagliflozinu

| Pos. [°2 Th.] | Interplanar distance [A] = 0.1 nm | Rel. Int. [%] |
| --- | --- | --- |
| 2.56 | 34.494 | 23.8 |
| 3.33 | 26.508 | 100.0 |
| 4.03 | 21.926 | 78.1 |
| 6.70 | 13.183 | 20.0 |
| 10.06 | 8.783 | 25.2 |
| 11.38 | 7.771 | 22.4 |
| 12.44 | 7.107 | 8.5 |
| 13.49 | 6.559 | 8.0 |
| 14.80 | 5.981 | 3.6 |
| 15.78 | 5.612 | 21.6 |
| 16.18 | 5.474 | 30.7 |
| 16.87 | 5.252 | 16.4 |
| 17.32 | 5.116 | 32.7 |
| 18.04 | 4.915 | 37.4 |
| 18.48 | 4.798 | 26.3 |
| 19.51 | 4.546 | 30.7 |
| 20.17 | 4.399 | 37.5 |
| 20.84 | 4.259 | 44.5 |
| 21.53 | 4.124 | 9.5 |
| 22.06 | 4.026 | 12.6 |
| 23.13 | 3.843 | 9.9 |
| 24.14 | 3.684 | 10.9 |
| 24.89 | 3.574 | 6.6 |
| 25.89 | 3.439 | 8.5 |
| 27.18 | 3.278 | 6.3 |
| 27.83 | 3.204 | 6.2 |
| 28.90 | 3.087 | 3.0 |

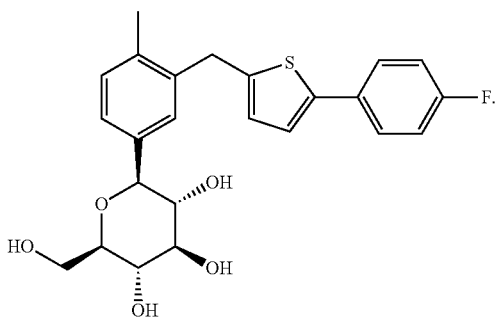

(I)

2. A method for preparing the crystalline form X-C of Canagliflozin defined in claim 1, comprising the steps of:
dissolving crystalline or amorphous Canagliflozin under boiling in a suitable etheric solvent selected from the group consisting of cyclopentyl methyl ether, t-butyl methyl ether and 2-methyltetrahydrofuran; drying the obtained solution by means of azeotropic distillation; cooling and/or adding an antisolvent in hot state wherein the antisolvent is selected from the group consisting of heptane, cyclohexane and hexane and then cooling the solution; and isolating the crystallized product.

3. The method for preparing in accordance with claim 2, wherein the procedure is carried out under an inert atmosphere of nitrogen or argon.

4. The method for preparing in accordance with claim 2, wherein the etheric solvent is cyclopentyl methyl ether and the antisolvent is heptane.

5. The method for preparing in accordance with claim 2, wherein the etheric solvent is 2-methyltetrahydrofuran and the antisolvent is heptane.

6. The method for preparing in accordance with claim 4 wherein the obtained solution is cooled down to a temperature in the range of 70-90° C. before the step of adding of the antisolvent.

7. The method for preparing in accordance with claim 2, wherein the etheric solvent is t-butyl methyl ether optionally with t-butanol.

8. The method for preparing in accordance with claim 7, wherein the obtained solution is cooled down to a temperature in the range of 50-60° C. before adding the antisolvent.

9. The method for preparing in accordance with claim 2, wherein after cooling, an inoculation crystal of form X-C is added to the solution.

10. The method for preparing in accordance with claim 2, wherein the distillation is carried out at a reduced pressure.

11. A method for preparing the crystalline form X-C of Canagliflozin defined in claim 1, wherein a tetraacetyl derivative of Canagliflozin of formula II is deacetylated in solvent comprising methanol in the presence of sodium methanolate,

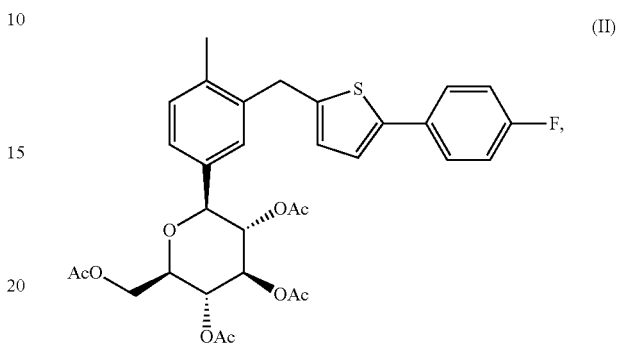

(II)

and after pH adjustment the solvent is replaced by distillation with an etheric solvent selected from the group consisting of cyclopentyl methyl ether, t-butyl methyl ether and 2-methyltetrahydrofuran, washing with water is carried out, followed by azeotropic drying and then the crystalline form X-C is prepared by cooling and/or adding an antisolvent in hot state, wherein the antisolvent is selected from the group consisting of heptane, cyclohexane and hexane; cooling the solution; and isolating the crystallized product.

12. The method for preparing in accordance with claim 11, wherein the method is carried out under an inert atmosphere of nitrogen or argon.

13. The method for preparing in accordance with claim 11, wherein the distillation is carried out at a reduced pressure.

14. A pharmaceutical composition comprising the crystalline form X-C of Canagliflozin in accordance with claim 1.

15. The method according to claim 2, further comprising adding a $C_1$-$C_5$ saturated aliphatic linear or branched alcohol to said etheric solvent during said step of dissolving said canagliflozin under boiling.

* * * * *